(12) United States Patent
Batchelor et al.

(10) Patent No.: US 12,201,343 B2
(45) Date of Patent: Jan. 21, 2025

(54) ADAPTIVE BLEND OF ELECTROSURGICAL CUTTING AND COAGULATION

(71) Applicant: GYRUS ACMI, INC., Westborough, MA (US)

(72) Inventors: Kester Julian Batchelor, Mound, MN (US); Jeffrey J. Nelson, Plymouth, MN (US); Richard J. Curtis, Corcoran, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 808 days.

(21) Appl. No.: 17/148,191

(22) Filed: Jan. 13, 2021

(65) Prior Publication Data

US 2021/0236189 A1    Aug. 5, 2021

Related U.S. Application Data

(60) Provisional application No. 62/968,030, filed on Jan. 30, 2020.

(51) Int. Cl.
*A61B 18/10* (2006.01)
*A61B 18/00* (2006.01)

(52) U.S. Cl.
CPC .... *A61B 18/10* (2013.01); *A61B 2018/00345* (2013.01); *A61B 2018/00607* (2013.01); *A61B 2018/0072* (2013.01); *A61B 2018/00767* (2013.01); *A61B 2018/00779* (2013.01); *A61B 2018/00791* (2013.01); *A61B 2018/00869* (2013.01); *A61B 2018/00875* (2013.01)

(58) Field of Classification Search
CPC ................................ A61B 18/12206
See application file for complete search history.

(56) References Cited

U.S. PATENT DOCUMENTS 9,265,560 B2    2/2016  Johnston
10,258,407 B2   4/2019  Ward et al.
(Continued)

FOREIGN PATENT DOCUMENTS

EP      2767249 A2      8/2014
WO   WO-03092520 A1    11/2003
(Continued)

OTHER PUBLICATIONS

"International Application Serial No. PCT/US2021/013443, International Search Report mailed Apr. 14, 2021", 7 pgs.
(Continued)

*Primary Examiner* — Michael F Peffley
*Assistant Examiner* — Samantha M Good
(74) *Attorney, Agent, or Firm* — Schwegman Lundberg & Woessner, P.A.

(57) ABSTRACT

An electrosurgical system can include a surgical device configured to adjust energy delivery in accordance with a specified cutting-to-coagulation relationship. The specified cutting-to-coagulation relationship can be determined based at least in part on an impedance or other parameter associated with tissue or an environment at or near the one or more electrodes. The specified cutting-to-coagulation relationship can be determined automatically (e.g., without requiring user input) and adaptively based on the sensing, such as in real-time as the therapy progresses.

8 Claims, 4 Drawing Sheets

(56) References Cited

U.S. PATENT DOCUMENTS

| | | | |
|---|---|---|---|
| 2012/0016359 A1* | 1/2012 | Podhajsky | A61B 18/1233 |
| | | | 606/34 |
| 2013/0035679 A1* | 2/2013 | Orszulak | A61B 18/1445 |
| | | | 330/69 |
| 2014/0128864 A1 | 5/2014 | Atwell | |
| 2017/0000551 A1* | 1/2017 | Ward | A61B 18/1233 |
| 2017/0319279 A1* | 11/2017 | Fish | A61B 18/12 |

FOREIGN PATENT DOCUMENTS

| | | |
|---|---|---|
| WO | WO-2017015287 A1 | 1/2017 |
| WO | WO-2021154505 A1 | 8/2021 |

OTHER PUBLICATIONS

"International Application Serial No. PCT/US2021/013443, Written Opinion mailed Apr. 14, 2021", 7 pgs.
"International Application Serial No. PCT/US2021/013443, International Preliminary Report on Patentability mailed Aug. 11, 2022", 9 pgs.

\* cited by examiner

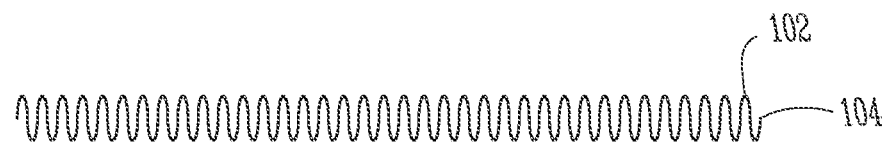
Fig. 1B
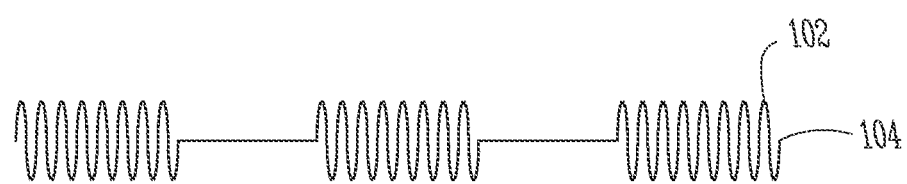
Fig. 1C
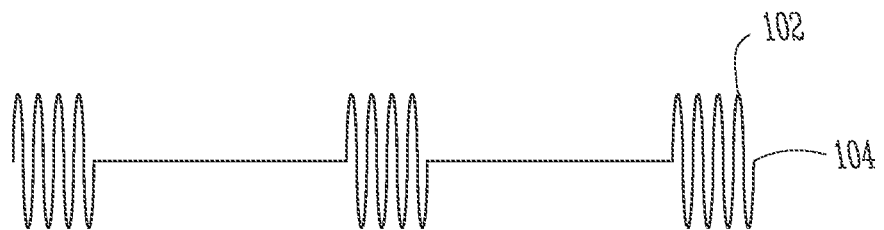

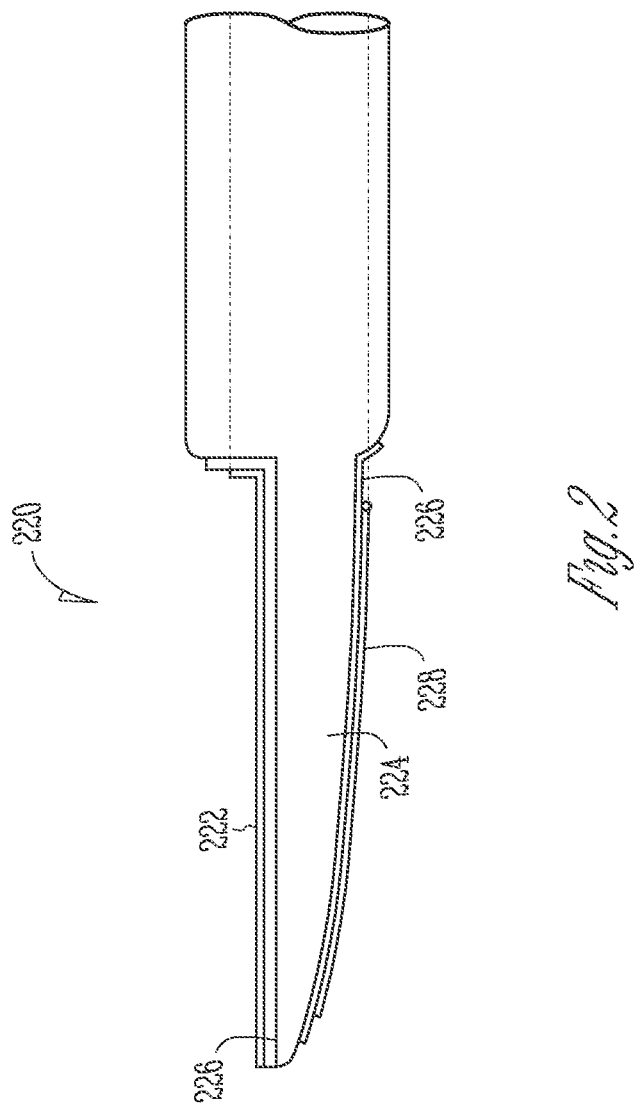

ADAPTIVE BLEND OF ELECTROSURGICAL CUTTING AND COAGULATION

CROSS-REFERENCE TO RELATED APPLICATION

This application claims the benefit of priority to U.S. Provisional Patent Application No. 62/968,030, filed Jan. 30, 2020, the contents of which are incorporated herein by reference in their entirety.

BACKGROUND

Electrosurgery uses the application of a high frequency alternating polarity electrical current, such as a radio frequency (RF) electrical current, to cut, coagulate, desiccate, or fulgurate tissue. The high frequency alternating current (AC) can be converted to heat by resistance as it passes through tissue. The result of heat buildup within the tissue can be used to cause tissue thermal damage, resulting in effects such as cutting or cautery of tissue. Electrosurgery can allow for high precision cutting in surgery with low blood loss.

The application of high frequency AC energy to tissue can heat the tissue through high frequency induced intracellular oscillation of ionized molecules, resulting in temperature elevation in the tissue. Cell death can occur in the tissue, for example, at about sixty degrees Celsius. At a range of about 60 to 99 degrees Celsius, coagulation of protein in the tissue can occur. When the temperature is above about boiling, vaporization of tissue cells can occur. Vaporization can be used to cut tissue.

Depending on the surgical procedure being attempted, and the type of tissue being treated with high frequency electrical current, the desired amount of tissue coagulation can differ compared to the desired amount of tissue cutting.

SUMMARY/OVERVIEW

For electrosurgical procedures, an electrode capable of both cutting and coagulation modes can be used. Depending on the type of tissue being treated, a particular ratio (or other relative measure) of cutting compared to coagulation may be preferred. For example, a surgeon may prefer a higher amount of cutting in vascular tissue, or a higher amount of coagulation in more electrically conductive tissue. An electrode capable of switching between cutting and coagulation can help provide a more hemostatic cut, such as in situations in which various different types of tissue are being treated. In some cases, the desired ratio of cutting-to-coagulation can change over the course of a surgery, such as depending on the environment of tissue in which the surgeon is working.

However, in many systems that use electrodes with both cutting and coagulation modes, the surgeon must select a set cutting-to-coagulation ratio before the surgery begins, and the ratio of cutting-to-coagulation remains the same throughout the procedure, regardless of whether the tissue type varies during the procedure.

For example, the surgeon may choose a setting with a more coagulation than cutting, which remains static regardless of the variation in tissue vasculature. In this case, if the surgeon is treating lightly vascularized tissue, the cutting speed may be slower, which may result in greater thermal damage to the tissue due to the pre-set static high coagulation amount.

Conversely, the surgeon may choose a setting with a more cutting than coagulation. In this case, the surgeon may be able to cut quickly through more vascularized tissue, but the procedure may still be slowed because the surgeon may need to return to the cut vascularized area to later provide additional coagulation without cutting from the device. In either case, the electrosurgical procedure can be slowed down due to the preset static ratio of cutting-to-coagulation, regardless of variation in tissue vascularity.

This document describes a method of adaptively blending the balance of coagulation and cutting in electrosurgery using an electrode with both coagulation and cutting capabilities. The adaptive blending can be based on one or more tissue characteristics, such as by reading a sensor input, such as the tissue impedance or resistance, and the changing the amount of coagulation relative to cutting, such as by changing a duty cycle between the coagulation and cutting electrosurgical signals delivered via the electrode.

For example, the device can sense and monitor feedback from the tissue being treated, and alter the ratio of cutting and coagulation accordingly. This can allow adaption of the amount of cutting and amount of coagulation, such as depending on the specific tissue type being treated.

In an example, an electrosurgical system can include a surgical device for at least partial insertion into a patient. The device can include a shaft, including a proximal portion and a distal portion and one or more electrodes located near the distal portion of the shaft, the electrodes configured to adjust energy delivery for tissue cutting relative to coagulation in response to at least one input signal that is based at least in part on a target tissue parameter, such as can be monitored near the one or more electrodes.

In an example, an electrosurgical system can include controller circuitry such as can be configured to receive a sensor signal from at least one sensor. The sensor signal can indicate a parameter corresponding to a target tissue. The controller circuitry can determine a specified cutting-to-coagulation relationship based on the sensor signal. The controller circuitry can produce an output signal, such as for delivery to an electrosurgical generator, such as to produce an electrostimulation energy waveform with the specified cutting-to-coagulation relationship.

In an example, an electrosurgery method of treating a patient can include sensing a parameter of target tissue and cutting and coagulating the target tissue in a specified relationship based at least in part on the sensed parameter of the target tissue.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 1B-1D illustrate diagrams of example electrical waveforms that could be used for electrosurgery.

FIG. 2 illustrates a schematic diagram of an example of a bipolar electrode that can be used for cutting and coagulation.

DETAILED DESCRIPTION

The present disclosure describes, among other things, systems and methods for manipulating the function of an electrosurgical electrode such as by altering the amount of coagulation and amount of cutting by the electrode such as based on the target tissue type.

The proposed device and methods discussed herein can help allow for adaptive changes in the cutting-to-coagulation relationship in an electrosurgical device, such as depending on the target tissue being treated with that device.

Figure 1A:
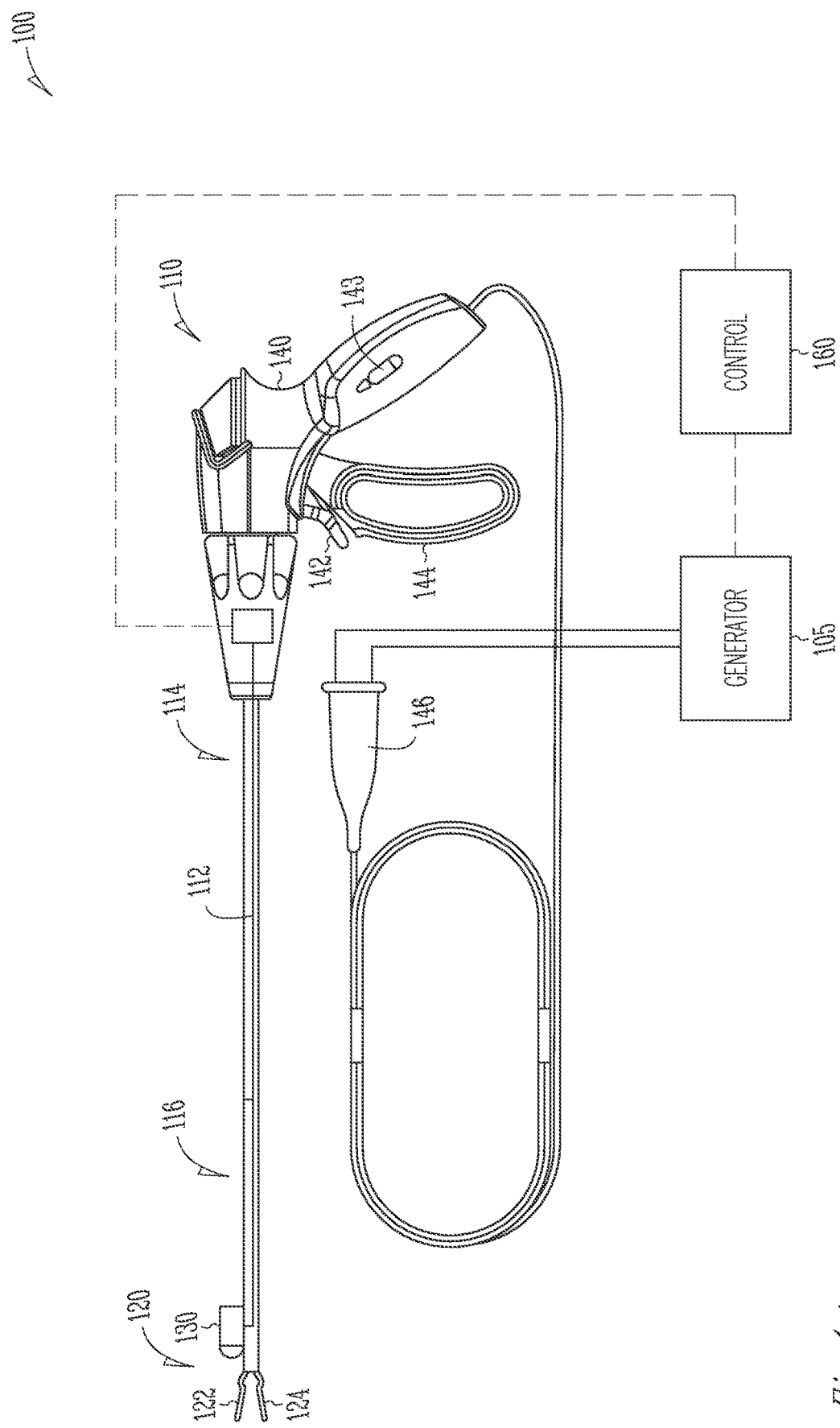
FIG. 1A illustrates a schematic diagram of an example of an electrosurgery system including a generator and an electrode for cutting and coagulation.

FIG. 1A illustrates a schematic diagram of an example of portions of an electrosurgery system 100, such as can include an electrosurgery device 110 with an electrosurgical electrode 120 such as for cutting and coagulation. The device 110 can be connected to an electrosurgical energy generator 105 and a controller 160.

The electrosurgery device 110 can include an elongated shaft 112 having a proximal portion 114 and a distal portion 116. The distal portion 116 can include an electrode 120, such as which can include a first electrode 122 and second electrode 124. The device 110 can also include one or more sensors 130. A proximal portion 114 of the device can be connected to a handpiece 140, such as with actuators 142, 143, and 144. The device 110 can also include a connector 146 such as can be configured to be connected to the generator 105.

The generator 105 can be external to but coupled to the electrosurgical device 110. The generator 105 can provide electrical energy to the electrode 120 of the electrosurgical device 110, such as through the electrical connector 146. The electrical generator 105 can produce a current deliverable by the electrode 120 such as for inducing a cutting or coagulation mode of electrosurgery, such as in response to an input signal for obtaining a variable specified relationship between cutting and coagulation, such as a ratio, a difference, or other adaptive relative measure between cutting and coagulation. The electrical generator 105 can be in communication with the controller 160, which can direct the application of electrosurgical energy to the electrode 120 in the electrosurgical device 110, such as according to a specific cutting-to-coagulation ratio.

The type and amount of electrical energy provided by the generator 105 can vary, such as depending on the desired amount of cutting and coagulation. The generator 105 can generate and automatically alter (e.g., without requiring user intervention) one or more electrosurgical waveforms, such as depending on the desired amount of cutting or coagulation, which can vary during the procedure, such as according to a tissue characteristic such as tissue type. Altering the electrosurgical energy waveforms can affect the depth and the rate at which heat is produced by the electrode 120, such as for automatically and adaptively changing the effect of the electrode 120 during surgery between cutting, coagulation or intermediate modes. The electrosurgical waveform produced, the voltage, and the power of the electrosurgical energy being delivered, and the size and surface area of the electrode 120, can affect the depth and the rate of producing heat, which, in turn, can alter the final effect on the target tissue.

For cutting tissue, the generator 105 can produce an electrosurgical energy waveform similar to a sine wave. Cutting can use a continuous electrosurgical energy waveform such as can be able to apply the maximum output power of the generator 105, if desired. For coagulating tissue, the peak current output can be greater than for cutting tissue, but with an intermittent or lower duty cycle waveform with lower average power than a cutting waveform. For cutting tissue, the peak voltage can be greater.

Cutting tissue can include resection and dissection. The use of a resection or dissection electrosurgical device could, for example, tear tissue and subsequently the surgeon could apply coagulation when the tissue environment becomes more fluid filled. Similarly, coagulating tissue can include desiccation and fulguration of tissue that may occur with similar electrosurgical devices, where treatment can be to stop bleeding through energy mediated procedures.

Various electrosurgical waveforms can be used for electrosurgical procedures. Rapid heating of tissue using a continuous waveform can result in vaporization, fragmentation, and ejection of tissue fragments, allowing for tissue cutting. Open circuit voltage of such electrical waveforms can be, for example, from about 300 to about 10,000 V peak-to-peak, inclusive. In some cases, rapid tissue heating can allow for explosive vaporization of interstitial fluid; if the voltage is sufficiently high, such as above 400 V peak-to-peak, the vapor can be ionized, sometimes resulting in conductive plasma allowing flow of electric current from the electrode via the plasma into the tissue.

FIGS. 1B-1D illustrate diagrams of example electrical waveforms that may be used for electrosurgery. FIG. 1B illustrates an example of a waveform that may be produced for cutting tissue. FIG. 1C illustrates an example of a waveform that may be produced for blended cutting and coagulation of tissue. FIG. 1D illustrates an example of a waveform that may be produced for coagulation of tissue. Each of the waveforms illustrated in FIGS. 1B-1D show a peak voltage 102 and an average voltage 104. In FIG. 1B, the waveform can be continuous to allow for sufficient tissue heating for cutting. In FIG. 1D, the waveform can be intermittent, to allow for coagulation. In FIG. 1C, the waveform can be intermittent, but with longer period to allow for a blended cutting and coagulation approach.

More precise electrosurgery can use pulsed waveforms. For example, pulses or bursts can be used to cut tissue. Pulses or bursts of electrical current can allow for heating and cutting of specific tissue, such as without or limiting heat spreading out to undesired target tissue, such as for allowing cutting of specific zones of tissue.

For tissue coagulation, the voltage can be dropped below the threshold for cutting modes. A higher voltage can produce a cutting output. A reduction of voltage can produce coagulation or desiccation type outputs. For tissue coagulation, for example, an electrosurgical waveform can include a sine wave that can be turned off and on in rapid succession. This can result in a slower (i.e., more controllable) heating process, such as can help cause the target tissue to coagulate instead of cut.

The duty cycle can be thought of as the portion of a period in which the system is active. In electrosurgery system 100, the duty cycle can be represented by the proportion of the ON time during which the electrical generator 105 is providing current to the device 110, relative to the total time, which includes both ON time and OFF time. An OFF time can include a much lower power delivery, below the range of tissue effects, not an absence of energy delivery. The duty cycle (proportion of ON time to OFF) time can be varied by the system 100, such as to allow control of the rate of heating target tissue being treated with the electrode 120 of the electrosurgical device 110.

Duty cycle can be represented as:

$$D = \frac{PW}{T}$$

Where D represents the duty cycle, PW is the pulse width of the waveform, or the active ON time of the pulse, and T is the total time period of the signal, where T includes both the ON time and the OFF time. For tissue coagulation, the duty cycle can be lower than for tissue cutting, as the pulse width of the waveform is often shorter in coagulation.

The electrosurgery device 110 can include an electrosurgery electrode such as for applying high-frequency alternating polarity electrical current to biological tissue, such as to cut, coagulate, desiccate, or fulgurate the tissue, such as may be desired by the surgeon treating the patient.

The electrosurgery device 110 can include a wet field device such as for wet field electrosurgery, such as in a saline solution, or in an open wound. In a wet field device, heating can result from an AC current passing between two electrodes. Heating can be the greatest where the current density is the highest. Thus, smaller surface area electrode can produce a greater amount of heat for treating tissue.

Wet field electrosurgical devices can provide both cutting and coagulation. Cutting can cause a small area of tissue to be vaporized or cut, while coagulation can cause a small portion of tissue to "dry," and stop bleeding. Coagulation can penetrate to a depth of about a few millimeters near the contact of the electrode. The coagulated tissue can remain temporarily physically intact after electrosurgery. The coagulated tissue can slough off or be replaced by fibrotic tissue after surgery. The ratio of cutting-to-coagulation in a given surgery can be adjusted, such as depending on the type of surgical procedure, and the type of target tissue being treated or the environment of the target tissue.

For tissue cutting, where the voltage level provided at the electrode is high enough, the heat generated can create a vapor pocket. If the temperature resulting from the electrode reaches above or about 400° C., a small section of the tissue can be vaporized or exploded, resulting in an incision or "cut."

For tissue coagulation, a lesser voltage level can leave tissue remaining grossly intact, but with smaller vessels sealed, such as can help for stopping capillary or small-arterial bleeding. The device 110 can allow for cutting or coagulation of tissue in various ratios, proportions, or other relative measures therebetween, such as can be automatically adaptively specified or adjusted, such as based upon a tissue type or characteristic.

In the device 110, the shaft 112 with the proximal portion 114 and the distal portion 116 can be sized, shaped, or arranged for partial insertion of the device 110 into a patient. The shaft 112 can include or can be made of one or more of a composite, plastic, or metallic material, or other material suitable for surgical applications. The proximal portion 114 can be near an operator, such as a surgeon, when the device 110 is in use. In some cases, the operator can be a robotic arm or other machine. The distal portion 116 can be sized, shaped, or arranged for insertion into the patient so that distal portion 116 is further from the operator during use.

In some cases, the shaft 112 can be sized, shaped, arranged, or otherwise configured for laparoscopy, in some cases, the shaft 112 can be shorter such as for open surgery applications. In some cases, such as for laparoscopy, the shaft can be long. In an open surgery application, the shaft can include a tissue interface element with cutting, coagulating, and sensing elements in or on a distal portion of that device.

Laparoscopy can include, for example, a surgical procedure in which a small incision is made, through which a device is inserted to diagnose or treat conditions. Laparoscopy is considered less invasive than regular open abdominal surgery. In the case of laparoscopy, an optical visualization or imaging device may also be inserted along with the device 110, such as to permit the optical device to allow viewing or imaging such as for the operator to observe the tissue. The optical visualization or imaging device can include a laparoscope, or viewing tube, such as with a camera. In some cases, the optical visualization or imaging device can include an ultrasound type imaging device for the operator to use during treatment.

By contrast, open surgery approaches can involve a larger incision, such as can allow more direct visual observation of cutting of skin and tissue, such to permit the surgeon to have a fuller view of the structures and organs involved in the procedure.

For example, in some applications, the shaft 112 can have a length in a range of 10 mm to 30 mm, inclusive. The shaft 112 can be narrow in a cross-section or a lateral dimension, such as for patient insertion via an incision. For example, the shaft 112 can have a cross-sectional or lateral width in a range of less than 6 mm, inclusive.

The electrode 120 can be located at or near the distal portion 116 of the shaft 112. The electrode 120 can include a bipolar or monopolar electrode such as for use in cutting tissue, coagulating tissue, or both. Both bipolar and monopolar electrodes can make use of high frequency electrical current such as to cut, coagulate, desiccate, or fulgurate tissue. With a monopolar electrode, the current can pass from the probe of the electrode to the target tissue and through the patient to a return pad attached or otherwise located elsewhere on the patient to complete the electrical circuit. In contrast, with a bipolar electrode configuration, current passes through the tissue between two more closely-spaced electrodes, such as between individual electrode arms of a forceps-type electrode. For this reason, a bipolar electrode configuration offers a shorter electrical pathway.

Monopolar or bipolar can refer to the number of active electrodes used in electrosurgery. In a monopolar electrosurgery, an active electrode can carry current to the tissue. The current can then spread through the body and be collected by a dispersive return electrode. In a bipolar configuration, the current passes through the tissue between tips of two active electrodes, such as between electrode tips of a bipolar forceps. In either configuration, the electrical generator 105 can be connected to both active and return electrodes, such as for sending and receiving current.

The electrode 120 can be one or more monopolar electrodes. In some cases, the electrode 120 can include single pole monopolar outputs, or multi-pole monopolar outputs. For example, the electrode 120 can be a monopolar electrode that can provide a blending cutting and coagulation output. The electrode 120 can, in some cases, include multiple monopolar electrodes.

The electrode 120 can be a bipolar electrode with first electrode 120A and second electrode 120B. The first and second electrodes 120A, 120B can have dissimilar characteristics, such as varying electrode surface area, thermal conductivity, or other characteristics, such as to configure the first electrode 120A as an active electrode (e.g., less surface area), and the second electrode 120B is configured as the return electrode (e.g., more surface area) in the electrosurgery device 110. The spacing between the first electrode 120A and the second electrode 120B, and the voltage supplied to the electrodes 120A, 120B, can be configured such as to permit current the pass through the target tissue between the first electrode 120A and the second electrode 120B. The electrode 120 can be configured such as to permit switching between tissue cutting and tissue coagulation. Various bipolar electrode configurations are discussed in more detail with reference to FIGS. 2A-2C below.

The electrode 120 can be used for treating target tissue in the patient. The target tissue can include vascular tissue, such as tissues containing blood vessels, such as arteries, capillaries, or veins. Examples of more vascular tissue can include muscle tissue. More highly vascularized tissue can include lung or liver tissue. More vascular tissue may benefit from a higher ratio or other relative amount of cutting compared to coagulation, such as to help break up the vascular tissue.

However, the target tissue can include a less vascular tissue and a more electrically conductive tissue. For example, where electrically conductive blood or saline is present in the target tissue region, the target tissue may benefit from a higher ratio or other relative amount of coagulation compared to cutting, such as to help inhibit or prevent excessive bleeding.

The one or more sensors 130 can be used to determine what type of target tissue or surgery environment is present, such as the type of tissue or tissue vascularity.

The one or more sensors 130 can be located at or near the distal end 116 of the shaft 112, and can be configured to detect a parameter of the target tissue or a parameter of the environment. The one or more sensors 130 can produce one or more sensor signals, such as can be based on and indicative of one or more such sensed parameters. For example, the one or more sensors 130 can include an electrical sensor, such as for measuring electrical conductivity, resistivity, impedance, phase angle, reactance, resistance, capacitance and inductance, or one or more combinations thereof, of the surgery environment. In some cases, the electrical sensor can include the electrode 120 itself or in combination with one or more other electrode or internal or external sensor or sensor interface components.

For example, the electrical sensor can be used to detect the real-valued or complex-valued electrical impedance or electrical conductance of the target tissue (e.g., electrical conductivity, electrical resistivity, electrical impedance, electrical conductance, phase angle, reactance, resistance, capacitance and inductance, or the like). Tissue containing or immersed in saline or blood can be more electrically conductive than a more vascular tissue environment. A more vascular tissue environment can be more electrically resistive than saline-bathed tissue. In general, skin tissue, bone, and fat (adipose) tissue can have relatively higher electrical resistance, while the intestinal wall tissue can have a lower electrical resistance. Muscle tissue can have higher electrical resistance than blood but less electrical resistance than fatty tissue.

In some cases, the electrical sensor can include an impedance sensor, such as can use the electrosurgical signal or a separate electrical test signal to deliver a specified current or voltage to the tissue and measure a responsive voltage or current indicative of tissue impedance, such as when the series impedance of the leads or electrodes are subtracted. A three-point or four-point probe or similar impedance sensing electrode arrangement can be used, such as to permit sensing of the response variable via a high input impedance sensing interface amplifier separate from the effects of the larger test or electrosurgical signal passing through the impedance of the leads connected to electrodes used for delivering such signals. For example, such a three-point or four-point probe can use bipolar electrodes for delivering the test or electrosurgical signal and can include one or more additional electrodes for sensing the response variable into the high input impedance sensing interface amplifier. Thus, the impedance sensor can include using the electrode 120, additional, or separate impedance sensing electrodes, or other impedance sensors can be provided. In some cases, an impedance value can be measured or sensed by monitoring the electrode itself without the use of an additional sensor.

Impedance information can also include phase angle information, such as can describe the phase relationship between current and voltage in an AC circuit, such as in a high frequency AC electrosurgery application. The phase angle can describe the phase difference between the voltage applied to the tissue impedance and the current driven through it. Because tissue impedance can include reactive components such as capacitance or inductance, the resulting current will either lag behind the applied voltage (e.g., phase shift due to inductive components) or lead the applied voltage (e.g., phase shift due to capacitive components). Phase angle can be determined, for example, between current and voltage at a given time by comparing the times corresponding to detected edges or other reference or threshold values of current and voltage.

Phase angle signal-processing circuitry can accomplish this comparison such as applying a technique such as a Discrete Fourier Transform (DFT). For example, samples of a signal being analyzed can be correlated point-by-point, such as with each of both a sine function and a cosine function. Arbitrarily, the cosine part can be called real, and the sine part can be called imaginary. If the signal being analyzed has no phase shift, the result of the DFT is 100% real. If the signal being analyzed has a 90-degree phase shift, the result of the DFT is 100% imaginary. If the result of the DFT has both a real and imaginary component, the phase angle can be calculated as the arctangent of a ratio of the imaginary and real values.

One or more electrical properties of the target tissue, such as conductivity, resistivity, impedance, or phase angle, can be sensed throughout electrosurgery, or during one or more "sensing pulses," such as can be sent out intermittently during electrosurgery.

In an example, the one or more sensors 130 can include a temperature sensor, such as for detecting a temperature of the target tissue or the surgery environment. The temperature sensor can, for example, detect a change in temperature in or near the target tissue. The temperature sensor can provide information about heat generated from the electrode 120, which, in turn, can be used in the automatic (e.g., permitting, but not requiring user intervention) adaptive determination of the ratio or other cutting-to-coagulation relationship of the electrosurgery therapy being delivered.

The temperature sensor can include a thermocouple, such as can include two dissimilar electrically conductive materials forming an interface therebetween. The thermocouple can produce a temperature-dependent voltage, such as a result of the thermoelectric effect between the materials at the interface. The resulting voltage can be interpreted to measure temperature or a change in temperature.

The one or more sensors 130 can include an optical sensor for detecting a light interaction (e.g., absorption, reflection, scattering, fluorescence, or the like) with target tissue or in the surgery environment. The optical sensor can be used to measure or detect a change in light in or near the target tissue. The light detected can be in the visible range, in the infrared (IR) range, in the ultraviolet (UV) range, in the radio wave range, or other wavelength of light, as appropriate.

For example, the one or more sensors 130 can include an electro-optical sensor that converts a detected light or a change in detected light to an electrical signal. The sensor can be configured as a position sensor, such as can activate when an object, such as tissue, blocks the path of and thereby interrupts light. The sensor can include a photoelectric sensor, such as can sense a distance to target tissue or another object, or the absence or presence of such object. One or more optical sensors can be included in addition to the electrode 120, such as can be mounted on or near the distal end 116 of the shaft 112.

The one or more sensors 130 can include a combination of one or more of these types of sensors, which can provide one or more resulting sensed signals to sensor interface or signal processing circuitry, such as can be included within or coupled to the controller 160. As discussed in detail below with reference to FIG. 3, the sensed signal(s) can be used to determine what kind of tissue or environment with which the electrode 120 and the device 110 are being used. Such tissue or environmental information can be used to automatically specify or alter the electrosurgical waveform being produced by the electrical generator 105, such as to alter the amount of cutting versus coagulation being done near the electrode 120, such as even during an application of electrosurgical energy.

The handpiece 140 can include one or more user-actuators, such as the actuators, 143, 144. In some cases, these can include one or more of levers, buttons, wheels, switches, triggers, or a combination thereof. One of the actuators 142, 143, 144, can provide a user-interface to control a first switch that selectively connects the electrode 120 to the generator 105 or other circuitry that can provide electrosurgical energy to the first electrode 120 such as for cutting and coagulation. Additional actuators, such as buttons, triggers, or other user-actuatable mechanisms can be included on the hand piece 140 of the device 110 or elsewhere for surgeon use, such as for direction and action of the electrode 120, movement of the shaft 112, or one or more other operations of the device 110.

The handpiece 140 can include or can be communicatively coupled to one or more alternative or additional buttons, triggers, or controls (e.g., a foot pedal), such as to allow the user to actuate energy delivery to the electrode 120 or other portions or components of the electrosurgical device 110, such as to actuate a forceps or a blade or a corresponding longitudinal extension/retraction translation or rotational mechanism upon which the electrode 120 rides.

The electrosurgical device 110, including the triggers on the handpiece 140, the electrode 120, and the one or more sensors 130, can be in communication with the controller 160. The generator 105 can also be in communication with the controller 160.

The controller 160 can include a processor and a memory such as to permit the controller 160 to communicate with and control the generator 105 to induce a specific cutting-to-coagulation relationship in the electrosurgical energy provided by electrode 120 of the electrosurgical device 110.

The controller 160 can be used to allow for both predictive and reactive control of the duty cycle produced by the generator 105. In a predictive scenario, the controller 160 can receive information about the tissue or environment type and set the ratio of cutting-to-coagulation accordingly. In a reactive scenario, if the controller 160 receives information indicating the tissue field subsequently gets drier than the initial setting suggests, the controller 160 can increase the cutting output time and voltage. Similarly, if the controller 160 receives information indicating bleeding, the coagulation output time can be increased.

The controller 160 can operate as a standalone device, or may be networked to other machines. The controller 160 can include a hardware processor, such as a central processing unit (CPU), a graphics processing unit (GPU), a hardware processor core, or any combinations thereof. The controller 160 can further include a memory, including a main memory and a static memory. The controller 160 can include an input device, such as a keyboard, a user interface, and a navigation device such as a mouse or touchscreen.

The controller 160 can additionally include a storage device, a signal generation device, a network interface device, and one or more sensors. The storage device can include a machine readable medium on which is stored one or more sets of data structure or instructions embodying or utilized by any one or more of the techniques described herein. The instructions may also reside, completely or at least partially, within the main memory, within static memory, or within the hardware processor during execution thereof by the controller.

In an example, one or any combination of the hardware processor, the main memory, the static memory, or the storage device may constitute machine readable media, that may include any medium that is capable of storing, encoding, or carrying instructions for execution by the controller 160 and that cause the controller 160 to perform any one or more of the techniques of the present disclosure, or that is capable of storing, encoding or carrying data structures used by or associated with such instructions. Non-limiting machine readable medium examples may include solid-state memories, and optical and magnetic media. The instructions on the controller 160 may further be transmitted or received over a communications network using a transmission medium via a network interface device.

In system 100, the controller 160 can receive one or more sensed signals such as from the one or more sensors 130. The one or more sensed signals can indicate a change in conductivity, resistivity, impedance, temperature, optical properties, or combinations thereof, of the target tissue or its surgical environment. The controller 160 can interpret the sensed signal(s), and determine an appropriate cutting-to-coagulation ratio or other relationship based on those sensed signal(s).

The controller 160 can then implement that appropriate cutting-to-coagulation ratio or other relationship, such as adaptively while the surgeon is conducting the surgery with the electrosurgical device 110, such as by directing the generator 105 to alter the electrosurgical waveform being produced to regulate the cutting-to-coagulation ratio or relationship. An example of a method of regulating the cutting-to-coagulation relationship is discussed in more detail with reference to FIG. 3 below.

FIG. 2 illustrates a schematic diagram of an example of a bipolar electrode cutting blade 220 such as can be used for electrosurgical cutting and coagulation. The bipolar electrode cutting blade 220 in FIG. 2 is an example of an electrode that could be used by the electrosurgical system 100.

The electrode cutting blade 220 can include, for example, a J-hook, cutting forceps, a needle, scissors, an L-hook, dissecting forceps, open forceps, a spatula or another type of surgical electrode. The cutting blade can include devices in which both the active cutting electrode and the return electrode are configured to enter the incision made by an instrument, such as to make lateral or axial incisions.

The electrode 220 can include, for example, a first electrode 222, a second electrode 224, an insulator 226, and a coagulation electrode 228. The first and second electrodes 222, 224, can have similar or dissimilar characteristics, such as varying surface area, thermal conductivity, or other properties.

The first electrode 222 can be configured to serve as an active electrode and the second electrode 224 can be configured to serve as a return electrode. The spacing between the first and second electrodes and the peak voltage supplied by an electrical generator to the first and second electrode 222 and 224 can be selected such that current between the first and second electrodes 222 and 224 passes through the target tissue.

Respective individual conductors can extend proximally from the electrodes 222, 224 along the shaft, such as toward the handpiece of the electrosurgical device, at which such conductors can be connected to an electrical energy source, such as to the generator 105. The poles of the electrodes 222, 224, can change polarity depending such as during device operation.

The first and second electrodes 222, 224, can be spaced, for example, about 0.25 mm to about 3.0 mm apart, inclusive. Such an arrangement can allow for a thermal difference of about at least 50° C. between the first electrode 222 and the second electrode 224. The second electrode can be maintained below a temperature of about 70° C. This can be accomplished, for example, by thermally insulating the second electrode 224 from the first electrode 222. Alternatively or additionally, thermal energy can be transferred away from the second electrode 224 such as by thermal conduction, forced cooling, a heat pipe, or one or more combinations thereof.

The third electrode 228 can be adapted to coagulate tissue. This coagulation electrode 228 can be insulated from the second electrode 226 using an insulator. The third electrode 228 can be thermally insulated so that it does not reach a prohibitively high temperature that is inconsistent with coagulation.

In coagulation, the first, second, and third electrodes, 222, 224, 228, can pass electrical current from one side to the other of the cutting blade 220, including passing electrical current through target tissue. This can allow for coagulation or hemostasis of such target tissue.

In cutting, the electrical current can pass between the electrodes 222, 224, in a higher current density compared to coagulation, such as to allow for cutting of target tissue. The electrodes 222, 224, 226, can having varying properties, such as differing surface areas or thermal conductivity. These differences can induce the passage of current through the tissue being treated between the electrodes.

Figure 3:
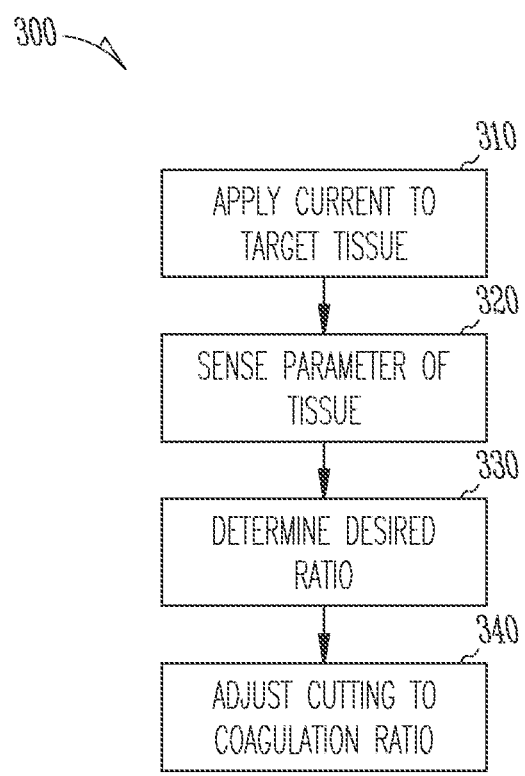
FIG. 3 illustrates a flow chart depicting an example of a method of regulating the cutting-to-coagulation ratio in an electrosurgery application.

FIG. 3 illustrates a flow chart depicting an example of a method 300 of regulating the cutting-to-coagulation ratio or relationship in an electrosurgery application, such as adaptively and automatically, without requiring user intervention during the regulating.

The method 300 can include applying electrosurgical energy such as an electrical current to target tissue (step 310), and sensing a parameter of the target tissue (step 320) or the surgical environment of the electrode, such as using one or more sensors, as discussed above with reference to FIG. 1. The electrosurgery can include treatment of the target tissue with the electrode by an operator such as a surgeon, or by a robotic or automated machine.

In some cases, such as impedance sensing, the sensing a parameter of the target tissue can include running an electrosurgical or a test AC current through the target tissue and detecting or measuring an electrical parameter, such as voltage, in response to the application of the current. The AC current can be, for example, the same electrosurgical AC current used to induce cutting or coagulation modes in the electrode, such as provided by the generator. Alternatively, a separate test current can be sent through the electrode for the purpose of sensing an electrical property. In either case, additional or separate electrodes may be used, such as for impedance sensing in a three-point probe or a four-point probe configuration, such as can help reduce the effect of lead impedance on the tissue impedance measurement. The electrical property sensed or calculated from a sensed signal can include, for example, conductivity, resistivity, impedance, phase angle, or one or more combinations thereof.

In method 300, at the beginning of surgery, the electrosurgical system can read one or more tissue properties, assess a tissue type, and set a default or initial cutting-to-coagulation ratio. In some cases, the surgeon may set the default or initial ratio prior to or at the beginning of surgery. In either case, the electrosurgical system can periodically or continuously monitor the tissue properties. During surgery, the system can initiate a change in the cutting-to-coagulation ratio based on instantaneous tissue conductivity or other tissue properties.

Some examples of electrical resistivity ranges associated with different types of tissue are listed in Table 1 below. The particular resistivity range of a target tissue can change depending on the specific tissue make-up, in addition to where and in which direction the resistivity is measured. Saline resistivity is provided for comparison.

TABLE 1

Electrical Resistivity of Tissue, Blood, and Saline

| Tissue Type | Resistivity (Ohms/cm) |
| --- | --- |
| Adipose (fat) tissue | 1800-2200 |
| Muscle tissue | 350-400 |
| Nerve tissue | 50-300 |
| Blood | 250-300 |
| Saline | 150-200 |

Alternatively or additionally, sensing a parameter of the target tissue can include detecting a change in temperature in the target tissue, such as using a thermocouple. In some cases, sensing a parameter of the target tissue can include applying visible or other light to the target tissue, and recording light scattering or one or more other responsive properties of the applied light. In some cases, sensing a parameter of the target tissue can include sensing a change in light applied to the tissue or the responsive property of the applied light.

In some cases, the sensed parameter can indicate or provide information about a tissue type, such as the examples in Table 1. In some cases, the one or more sensors can detect more than one signal from the tissue, from which the information about or indication of a tissue type can be obtained.

Additionally or alternatively, the method could include collecting sensor data more often in one type of tissue environment than another. For example, if the surgeon is irrigating with saline, additional data regarding impedance (or another property) can be collected, potentially collecting more sensed data points closer together, such as to allow for additional sensing and monitoring in a saline irrigated tissue environment. This may allow for quicker and more reactive changing of the cutting to coagulation ratio during surgery in a particular tissue environment.

A controller or other signal processor circuitry, such as with a processor and memory, can process the received the sensed signal information about the tissue or surgical environment from the one or more sensors, such as for use in controlling the electrical generator to provide an appropriate cutting-to-coagulation relationship for treating the target tissue (step 330). This can be done, for example, with a look-up table, curve matching, comparing sensed data to a library of data, or other methods.

For example, the processor can than produce one or more sensed values associated with the target tissue. The processor can subsequently or simultaneously compare the produced sensor values with a library of sensor data and to determine what ratio of cutting-to-coagulation can be appropriate based on the sensor information.

The controller can issue one or more control signals to the electrical generator such as to establish or adjust the cutting-to-coagulation ratio (step 340). In some cases, the controller can suggest to a user, such as through a user interface or other signal, a suggested cutting-to-coagulation ratio or change in the cutting-to-coagulation ratio. The user can then accept or reject the suggested cutting-to-coagulation ratio or change in the cutting-to-coagulation ratio. In some cases, the controller can automatically induce the change in the electrical generator without requiring user input. In either case, the cutting-to-coagulation ratio change can, in turn, change the voltage or current applied by the electrical generator to the electrosurgical device being used to treat the target tissue.

In some cases, a modifier can be included in the electrosurgical system, such as in the electrosurgical device or the generator. Such a modifier could limit the range of cutting to coagulation ratios applicable to the surgery being performed. For example, the amount of voltage or current produced could be capped. For instance, a variable resistor could be used to artificially change the range of resistance detected by the one or more sensors, resulting in a limited change in the cutting-to-coagulation ratio output.

In some cases, the controller can learn from previous settings. For example, the controller could receive information indicating the tissue is mesentery, and the surgical procedure or tissue thus required more voltage. Later in the same procedure, or in a subsequent procedure, the system then could be more inclined to produce a higher voltage, resulting in a higher amount of cutting and a lower amount coagulation output.

For example, where the sensor data indicates a highly electrically conductive tissue, the controller can specify a ratio that biases coagulating tissue over cutting tissue. Where the sensor data indicates a highly vascular tissue, the controller can specify a ratio that biases coagulating tissue over cutting tissue.

The method can occur once in a surgery, at specified time markers throughout the surgery, when the physician indicates that a new analysis is desired, continuously, intermittently, or at periodic or other recurring time intervals throughout the surgery. The sensor and controller can be programmed to sense one or more parameters throughout the ongoing surgery, so that when the surgeon switches surgical areas, or the tissue becomes bloody or is irrigated with saline, the electrical generator can adaptively change the cutting-to-coagulation ratio accordingly.

Detection of different surgical areas can also include a change in the electrode itself, such as closing or opening of forceps, extension or retraction of a blade, or initiation of irrigation to a tissue area. In the case of one of these or other events, the system can be programmed to change the ratio of cutting to coagulation, or to re-measure the impedance or other tissue characteristic to suggest or induce a changed relationship of cutting to coagulation.

In an example, the controller can cause the electrode to alternate between cutting as coagulation. For example, in a given procedure, there may be ten time slots. The controller can, based on sensed information and other procedural information, pick a number of time slots for cutting, and a number of time slots for coagulation. This may be, for example, three cutting time slots and seven coagulation time slots. These numbers could be adjusted depending on the surgery being performed, and the data received by the processor indicating parameters of the tissue or the surgical area. The order of these time slots could also be changed depending on this information. In this case, the ratio of cutting to coagulation may not change, but the nature of the duty cycle may change. The controller can change the duty cycle as the electrosurgery progresses, based on a tissue parameter. This can be changed continuously throughout the electrosurgery, intermittently during the electrosurgery, or at periodic or other recurring time intervals. The relative measurements can be automatically adaptively specified or adjusted, such as based on a tissue type or characteristic.

Examples

Each of these non-limiting examples can stand on its own, or can be combined in various permutations or combinations with one or more of the other examples.

Example 1 can include an electrosurgical system including a surgical device for at least partial insertion into a patient, the device including a shaft, including a proximal portion and a distal portion; and one or more electrodes located near the distal portion of the shaft, the electrodes configured to adjust energy delivery for tissue in accordance with a specified cutting-to-coagulation relationship that is based at least in part on a target tissue parameter near the one or more electrodes.

Example 2 can include Example 1, comprising at least one sensor located at or near the distal portion of the shaft, the at least one sensor configured to sense the target tissue parameter of target tissue and produce a sensor signal based on the target tissue parameter.

Example 3 can include any of Examples 1-2, wherein the at least one sensor includes at least one of the electrodes.

Example 4 can include any of Examples 1-3, further including an electrosurgical generator configured to be coupled to the surgical device, the electrosurgical generator configured to produce an electrosurgical energy waveform in accordance with the specified cutting-to-coagulation relationship; and controller circuitry configured to: receive the sensor signal from the at least one sensor, determine the specified cutting-to-coagulation relationship based on the sensor signal, and direct the electrosurgical generator to provide an electrosurgical energy waveform in accordance with the specified cutting-to-coagulation relationship.

Example 5 can include any of Examples 1-4, wherein the least one sensor comprises a temperature sensor for detecting a temperature of target tissue.

Example 6 can include any of Examples 1-5, wherein the least one sensor comprises an optical sensor for detecting a light interaction with target tissue.

Example 7 can include any of Examples 1-6, wherein the at least one sensor comprises an electrical sensor for detecting conductivity of target tissue.

Example 8 can include any of Examples 1-7, wherein the at least one sensor comprises an electrical sensor for detecting resistivity of target tissue.

Example 9 can include any of Examples 1-8, wherein the at least one sensor comprises an electrical sensor for detecting impedance of target tissue.

Example 10 can include any of Examples 1-9, wherein the at least one sensor comprises circuitry for detecting phase angle.

Example 11. An electrosurgical system including controller circuitry configured to: receive a sensor signal from at least one sensor, the sensor signal indicating a parameter corresponding to a target tissue; determine a specified cutting-to-coagulation relationship based on the sensor signal; and produce an output signal for delivery to an electrosurgical generator to produce the specified cutting-to-coagulation relationship.

Example 12 can include Examples 11, further comprising a surgical device that comprises: a shaft, including a proximal portion and a distal portion; and an electrodes located at or near the distal portion of the shaft, the electrode configured to be operated in the specified cutting-to-coagulation relationship according to an output signal from the electrosurgical generator according to the output signal from the controller circuitry.

Example 13 can include any of Examples 11-12, wherein the surgical device further comprises at least one sensor located at or near the distal portion of the shaft, the at least one sensor configured to sense the parameter corresponding to the target tissue and produce the sensor signal based on the parameter.

Example 14 can include any of Examples 11-13, wherein the at least one sensor includes the electrode.

Example 15 can include any of Examples 11-14, further comprising the electrosurgical generator coupled to the surgical device, the electrosurgical generator configured to produce the output signal at the specified cutting-to-coagulation relationship.

Example 16 can include any of Examples 11-15, wherein the parameter comprises at least one of tissue impedance, tissue conductivity, tissue temperature, light interaction with tissue, tissue reactance, tissue resistance, tissue capacitance, tissue inductance, or one or more combinations thereof.

Example 17 can include any of Examples 11-16, wherein the parameter comprises phase angle between a voltage and a current applied to the tissue via the electrodes.

Example 18 can include an electrosurgery method of treating a patient, including sensing a parameter of target tissue; and cutting and coagulating the target tissue in a specified relationship based at least in part on the sensed parameter of the target tissue.

Example 19 can include Example 18, wherein cutting and coagulation the target tissue comprises applying a supply of electromagnetic energy to a surgical electrode treating the target tissue based on the specified relationship.

Example 20 can include any of Examples 18-19, further comprising continuously sensing the parameter of the target tissue, and adjusting the specified relationship based on the parameter as surgery progresses.

Example 21 can include any of Examples 18-20, further comprising periodically sensing the parameter of the target tissue, and adjusting the specified relationship based on the parameter as surgery progresses.

Example 22 can include any of Examples 18-21, wherein the cutting-to-coagulation relationship is adjusted as the therapy progresses without requiring user adjustment.

Example 23 can include any of Examples 18-22, further comprising biasing toward cutting the target tissue when the sensed parameter indicates a highly conductive tissue.

Example 24 can include any of Examples 18-23, further comprising biasing toward coagulating the target tissue when the sensed parameter indicates a highly vascular tissue.

Example 25 can include any of Examples 18-24, wherein sensing the parameter of the target tissue comprises sensing a characteristic of an impedance associated with the target tissue or its surgical environment.

Example 26 can include any of Examples 18-25, wherein sensing the parameter of the target tissue comprises detecting a change in temperature in the target tissue.

Example 27 can include any of Examples 18-26, wherein sensing the parameter of the target tissue comprises applying visible light to the target tissue, and recording light scattering properties of the applied visible light.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An electrosurgical system comprising:
   a bipolar surgical forceps device for at least partial insertion into a patient, the bipolar surgical forceps device comprising:
   a shaft, including a proximal portion and a distal portion;
   a forceps extending from the distal portion of the shaft, the forceps including a first jaw and a second jaw;
   two electrodes located on the forceps opposite each other on the first jaw and the second jaw, the two electrodes configured to adjust energy delivery for tissue in accordance with a specified blended cutting-to-coagulation relationship that is based at least in part on a target tissue parameter near at least one of the two electrodes;
   a sensor located at or near the distal portion of the shaft, the sensor configured to sense the target tissue parameter of target tissue and produce a sensor signal based on the target tissue parameter, the sensor including at least one of the two electrodes and is configured to recurrently sense the target tissue parameter as a surgical procedure progresses; and
   a controller configured to receive the sensor signal and to recurrently automatically adjust the specified blended cutting-to-coagulation relationship in real-time using the sensor signal based on the target tissue parameter as recurrently sensed as the surgical procedure progresses.

2. The electrosurgical system of claim 1, further comprising:
   an electrosurgical generator configured to be coupled to the surgical device, the electrosurgical generator configured to produce an electrosurgical energy waveform in accordance with the specified cutting-to-coagulation relationship.

3. The electrosurgical system of claim 1, wherein the least one sensor comprises a temperature sensor for detecting a temperature of target tissue.

4. The electrosurgical system of claim 1, wherein the least one sensor comprises an optical sensor for detecting a light interaction with target tissue.

5. The electrosurgical system of claim 1, wherein the at least one sensor comprises an electrical sensor for detecting conductivity of target tissue.

6. The electrosurgical system of claim 1, wherein the at least one sensor comprises an electrical sensor for detecting resistivity of target tissue.

7. The electrosurgical system of claim 1, wherein the at least one sensor comprises an electrical sensor for detecting impedance of target tissue.

8. The electrosurgical system of claim 1, wherein the at least one sensor comprises circuitry for detecting phase angle.

* * * * *

UNITED STATES PATENT AND TRADEMARK OFFICE
CERTIFICATE OF CORRECTION

| | | |
|---|---|---|
| PATENT NO. | : 12,201,343 B2 | Page 1 of 1 |
| APPLICATION NO. | : 17/148191 | |
| DATED | : January 21, 2025 | |
| INVENTOR(S) | : Batchelor et al. | |

It is certified that error appears in the above-identified patent and that said Letters Patent is hereby corrected as shown below:

In the Claims

In Column 18, Line 23, in Claim 3, after "the", insert --at--

In Column 18, Line 26, in Claim 4, after "the", insert --at--

Signed and Sealed this
Eighth Day of April, 2025

Coke Morgan Stewart
*Acting Director of the United States Patent and Trademark Office*